United States Patent [19]

Riddle, Jr.

[11] Patent Number: 5,641,947
[45] Date of Patent: Jun. 24, 1997

[54] RECEPTACLE REMOVEABLY ATTACHED TO A WEIGHING SCALE FOR DISPOSAL OF MEDICAL WASTE

[76] Inventor: Michael C. Riddle, Jr., 8901 Wisconsin Ave. BEQ61 Rm. 129WB, Bethesda, Md. 20889

[21] Appl. No.: 612,482

[22] Filed: Mar. 7, 1996

Related U.S. Application Data

[63] Continuation of Ser. No. 398,433, Mar. 3, 1995, abandoned.

[51] Int. Cl.$^6$ ............................ G01G 21/00; G01G 21/28
[52] U.S. Cl. ........................ 177/126; 177/245; 177/124; 177/180; 220/404; 248/147
[58] Field of Search ............................ 220/403, 404; 248/147; 177/147, 180, 181, 245, 238, 262, 1, 60, 124, 160, 118, 126

[56] References Cited

U.S. PATENT DOCUMENTS

| | | | |
|---|---|---|---|
| 570,561 | 11/1896 | O'Brien | 226/19 |
| 736,553 | 8/1903 | Schmidt | 226/19 |
| 821,929 | 5/1906 | Dawson | 226/19 |
| 826,771 | 7/1906 | Edwards et al. | 226/19 |
| 1,019,685 | 3/1912 | Millard | 226/19 |
| 1,072,897 | 9/1913 | Amacher | 226/19 |
| 1,146,061 | 7/1915 | Garnier | 226/19 |
| 1,230,734 | 6/1917 | Lilja | 226/19 |
| 1,462,983 | 7/1923 | Schaper | 226/19 |
| 1,520,372 | 12/1924 | Syers | 226/19 |
| 2,069,499 | 2/1937 | Marin et al. | 177/245 |
| 2,626,093 | 1/1953 | Barber | 226/19 |
| 3,321,036 | 5/1967 | Keenan et al. | 177/245 |
| 4,422,548 | 12/1983 | Cheesman et al. | 177/245 X |
| 4,444,355 | 4/1984 | Cary | 220/403 X |
| 4,753,367 | 6/1988 | Miller et al. | 220/404 |
| 4,765,579 | 8/1988 | Robbins, III et al. | 220/404 X |
| 4,907,710 | 3/1990 | Bulkens | 220/404 X |
| 4,913,308 | 4/1990 | Culbertson | 220/404 |
| 4,953,740 | 9/1990 | Koda | 220/404 X |
| 5,056,679 | 10/1991 | Lonczak | 220/404 |
| 5,112,319 | 5/1992 | Lai | 177/45 X |
| 5,328,028 | 7/1994 | Hale et al. | 220/403 X |
| 5,363,980 | 11/1994 | Mulcahy | 220/404 |
| 5,385,259 | 1/1995 | Bernstein et al. | 220/404 |

OTHER PUBLICATIONS

Color copies of two photographs of waste container currently used. No Date Given.

*Primary Examiner*—Michael L. Gellner
*Assistant Examiner*—Randy W. Gibson
*Attorney, Agent, or Firm*—Vinson & Elkins L.L.P.

[57] ABSTRACT

An apparatus for hazardous waste disposal includes a container for holding a disposable flexible plastic bag without putting tear strain on the bag, and a weighing device for placement under the container so that the weight of the bag may be monitored as it is being filled with hazardous waste.

2 Claims, 3 Drawing Sheets

RECEPTACLE REMOVEABLY ATTACHED TO A WEIGHING SCALE FOR DISPOSAL OF MEDICAL WASTE

This application is a continuation, of application Ser. No. 08/398,433, filed Mar. 3, 1995 abandoned.

FIELD OF THE INVENTION

The present invention is directed generally to a waste disposal apparatus, more specifically to a waste disposal apparatus which permits safe filling of a disposable plastic bag with the optimum weight of hazardous waste by allowing the weight of the bag to be monitored during filling.

BACKGROUND OF THE INVENTION

Many industries produce hazardous waste which must be disposed of in the proper manner. Hospitals and other health care or research facilities must dispose of test tubes containing blood, microhematocrit tubes, contaminated dressings, blood products, and other hazardous wastes. The safety of the health care workers handling the waste is of the utmost importance. However, the costs of disposal must be minimized as well.

The current method for disposing of hazardous medical waste involves filling disposable plastic bags to a preset weight, placing these plastic bags in bum boxes, and sending the filled bum boxes to a waste disposal facility for incineration. Most facilities have adopted the use of red heavy duty polyethylene 30 gallon bags. These bags measure approximately 43×11×19 inches. Health care facilities generally pay for hazardous waste disposal by the bag rather than by the pound, and therefore prefer that each bag be filled as close as possible to a predetermined weight. Underfilling of bags results in increased expenditure for waste disposal. However, the waste disposal facility generally will not accept bags which exceed a predetermined weight. Most waste disposal facilities impose a 30 pound weight limit per bag. Maximum bum efficiency cannot be achieved for overweight bags. Therefore, if a bag is overfilled a health care worker is required to hand transfer some waste from the overweight bag to another bag. This procedure poses extreme risk to the person handling the hazardous waste, particularly for wounds from broken test tubes which can result in the contraction of potentially fatal diseases.

The waste disposal containers currently used at many hospitals and health care facilities generally consist of large transparent square containers with cumbersome hingedly attached lids. Such lids are typically poorly attached and they break easily. Many problems have been encountered in using the waste disposal containers. First, the dimensions of the containers have caused tear strain on the disposable plastic bags which are typically stretched to fit over the top of the square container. Torn plastic bags may allow waste to escape when the bag is removed from the square container. Secondly, when spills of hazardous waste occur the square containers have been difficult to clean because of their depth. Opening of the cumbersome lid on the square container each time hazardous waste is added to the plastic bag has proven to be inconvenient. Thus, the lid is either left open or permanently removed. When the lid is left open, its entire weight dangles from the hinge, damaging or breaking the hinge. Permanent removal of the lid from the square container potentially exposes health care workers to airborne contaminants. There is a need for a lid which can be opened easily and left open without damaging the container. Finally, there has been no method for checking the weight of the filled plastic bag without removing it from the square container for weighing. If the bag is underweight, it must be once again stretched to fit back in the square container. If it is overweight, waste must be hand transferred to a new plastic bag. This additional handling of the plastic bag and the waste increases the risks to health care workers.

Thus, there is a significant need for an apparatus which allows the weight of the plastic bag to be monitored while the plastic bag is being filled with hazardous waste. Such an apparatus would eliminate the risky practice of hand transferring waste from one bag to another. There is also a need for a hazardous waste disposal apparatus which is designed to hold a disposable plastic bag without putting tear strain on the plastic bag and which allows the plastic bag to be filled to its optimum capacity. It would also be desirable for the square container to be transparent for spill detection and easily disassembled for cleaning. A lid which opens easily and is convenient to use would provide increased safety.

SUMMARY OF INVENTION

The present invention is directed to a waste disposal apparatus that satisfies the need for a safe and accurate way to fill disposable plastic bags with hazardous wastes such that the plastic bags, when full, are at a predetermined weight. Use of the present invention will save potentially thousands of dollars each year by eliminating underweight bio-hazardous bum boxes. Use of this invention will also maximize safety for workers who place waste in the disposable plastic bag within the container which is used to hold the plastic bag as it is being filled.

The apparatus of the present invention comprises a container constructed and arranged to hold a disposable flexible plastic bag without tearing the bag and a weighing device usable with the container such that the stability of the container or the container's ability to hold plastic bags is not compromised. An advantage of this apparatus is that it prevents underfilled and overfilled bags and thus provides for minimum cost of disposal and maximum bum efficiency. Another advantage of the present invention is that the disposable plastic bags do not experience tearing strain or stretch. A further advantage of this apparatus is that it is made of detachable clear acrylic parts to facilitate detection of spills and provide for easy cleaning and sanitizing. Another advantage of the present invention is that the container lid opens and closes easily without damaging the container and thus encourages the user to keep the container lid shut when wastes are not being added to the bag. This feature decreases the chance for escape of airborne contaminants.

BRIEF DESCRIPTION OF DRAWINGS

These and other features, aspects and advantages of the present invention will become better understood with regard to the following description, appended claims and accompanying drawings where:

DETAILED DESCRIPTION OF PREFERRED EMBODIMENTS

Figure 1:
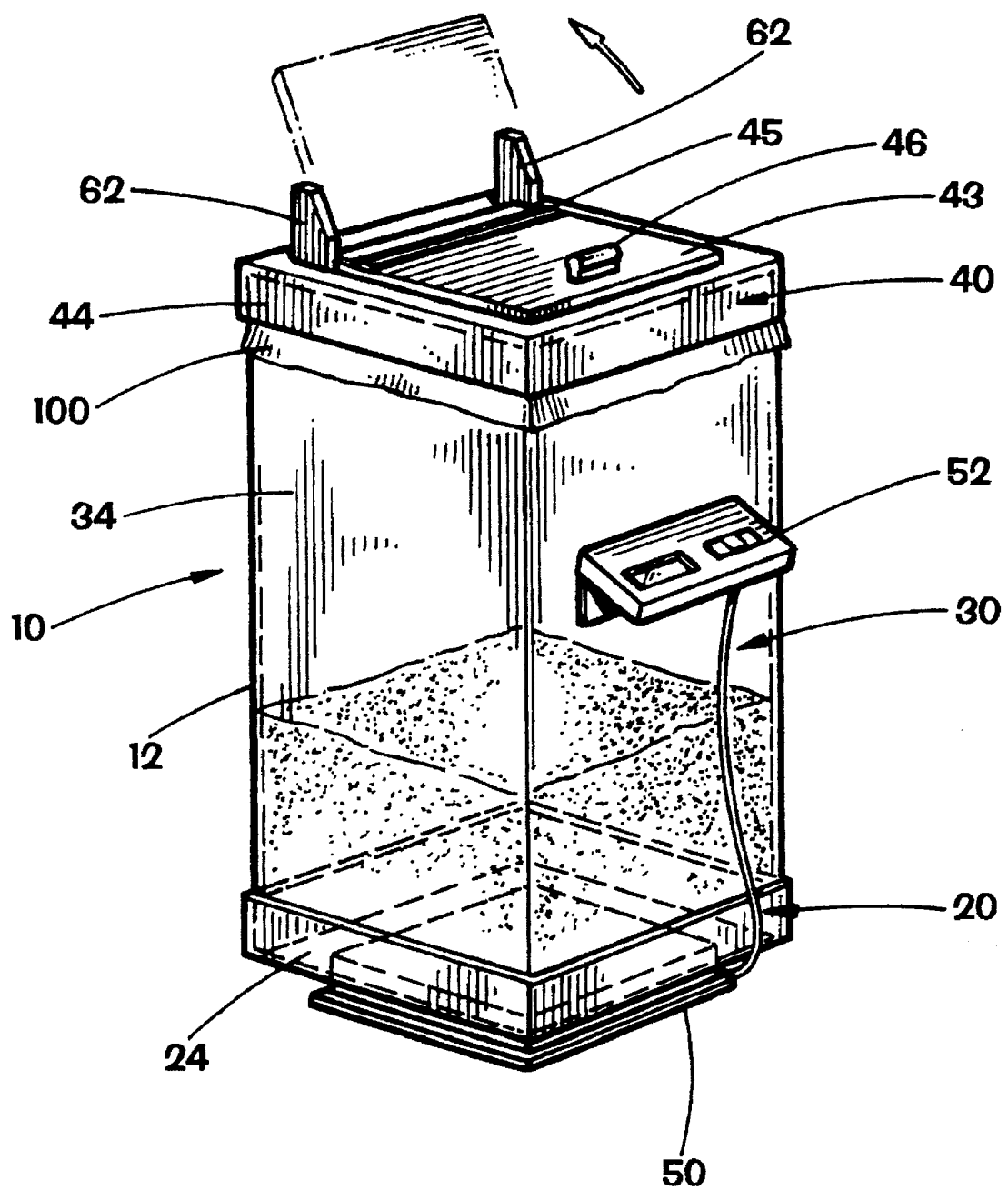
FIG. 1 is a perspective view of the assembled apparatus of the present invention with a disposable flexible plastic bag in place.

In FIG. 1, the waste disposal apparatus generally 10 is shown in its assembled form with a disposable plastic bag 100 placed within the container 12. The container 12 has three detachable parts, a base 20, a body 30, and a cover 40. A scale or weighing device 50 is placed under the container and a digital readout display 52 is attached to the body 30 of the container 12.

Figure 2:
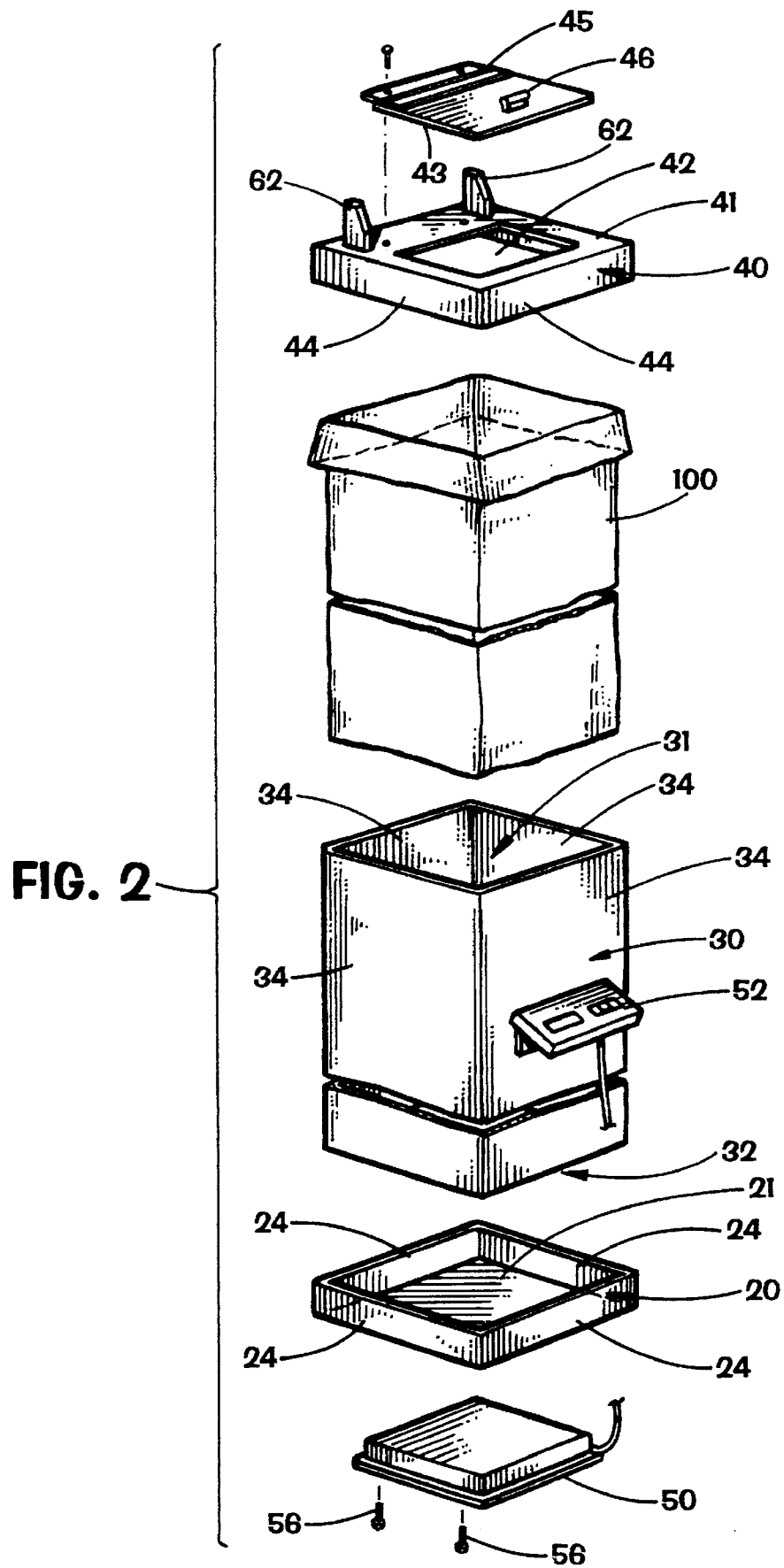
FIG. 2 is an exploded perspective view of the apparatus showing its various component parts and their relation to one another.

In FIG. 2, the base 20 has a bottom substantially planar surface 21 and four sides 24. The base 20 is sized so that its inside diameter is slightly larger than the outside diameter of the body 30 thereby allowing the body 30 to slide into the base 20 providing a snug fit. The body 30 has an open top end 31 and an open bottom end 32. The body 30 also has 4 substantially planar sides 34. The inside diameter of the cover 40 is sized to be larger than the outside diameter of the body 30 thus providing room to accommodate a disposable plastic bag 100. The cover 40 has a substantially planar surface 41 and four sides 44. In the preferred embodiment of this invention, the cover, base, and body are constructed from 3/8 inch thick clear acrylic sheets. The transparency of the container 12 allows spills to be detected. The clear acrylic material also serves as a beta radiation blocker. While a transparent construction provides easy detection of spills, the container could be made from an opaque material.

The weighing device or scale 50, is placed under the base 20. The scale 50 should have a capacity sufficient for accurate detection of the ideal predetermined weight of hazardous waste suitable for putting into a burn box (not shown). The preferred embodiment uses a Model PS 400L 400 pound scale. The scale 50 is calibrated to read zero when the fully assembled container with an empty disposable plastic bag inside is placed on the scale 50. The base 20 may be permanently attached to the scale 50 by means of threaded fasteners 56. In the preferred embodiment the scale 50 includes a digital readout display 52. The digital readout display 52 used in the preferred embodiment displays weight in 0.5 pound increments. The digital display 52 may be attached to the body 30 by means of adhesive, hook and loop, or threaded fasteners. The digital readout display allows the weight of the waste in the bag to be known at all times. Other methods for displaying the weight measurement could include a manual weighing device, or beam, such as is used on a doctor's scale. An alarm, either an audible tone or a flashing visual display, could be used in conjunction with the digital display or alone. The alarm would provide a signal when the ideal predetermined weight of hazardous waste is reached.

While the container of the preferred embodiment is constructed from substantially planar sheets of clear acrylic plastic for cost effectiveness, the container could be molded to be any shape, round, oval, etc. The important feature is that the dimensions of the container 12 be such that the plastic disposable bag 100 is not overstretched or torn. The inventor has found that a square container, having outside dimensions of 29½ inches in depth and a top open end that is 15½ inches by 15½ inches, will hold a standard 30 gallon red plastic disposable bag without overstretching or tearing the bag. The plastic bag 100 is secured within the container 12 by folding the sides of the top of the bag 100 over the top open end 31 of the body 30 and placing the cover 40 over the body 30 thus, sandwiching the bag in between the cover 40 and the body 30.

FIG. 2 also shows the preferred embodiment of the cover 40 of the present invention. In the preferred embodiment an opening 42 is made in the top surface 41. A lid 43 which is larger than the opening 42 is sized to cover the opening 42 and overlap with the edges of the surface 41 around the opening 42. The lid 43 is attached to the surface 41 by a hinge 45. For durability of construction, a stainless steel hinge is used. The lid 43 also has a handle 46. Two stops 62 are attached to the surface 41 of the cover 40 behind the hinge 45. When the lid 43 is open ii can rest against the stops 62. This prevents stress on the hinge 45 and provides convenient opening and closing of the lid 43. The stops 62 may be attached by adhesive or threaded fasteners. One stop could also be used, however, two stops are preferred for best support of the lid. Magnetic strips or hook and loop fasteners could be added to the lid and the stops for a more secure holding of the lid 43 in the open position. Other alternative embodiments may include using a vertical support member similar to that used to hold the hood of a motor vehicle open, to hold the lid 43 open.

Figure 3:
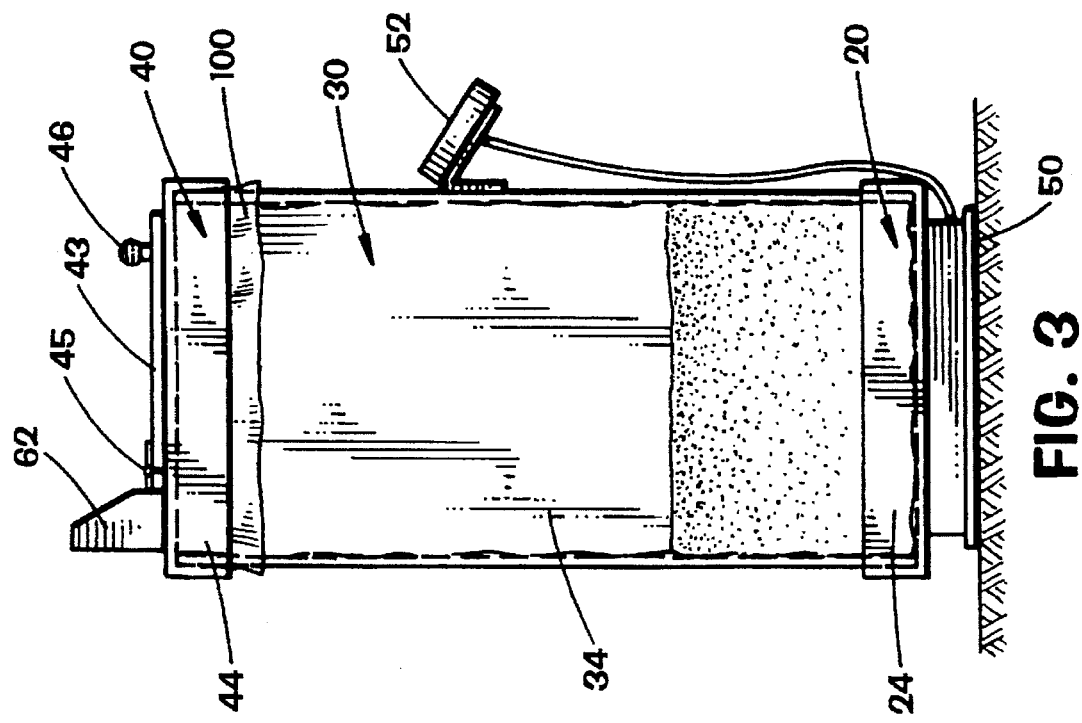
FIG. 3 is a side view of the assembled apparatus.

FIG. 3 shows a side view of the assembled apparatus 10. In FIG. 3, the attachment of the digital readout display 52 to the body 30 can be seen. Also, the placement of the scale 50 beneath the container is visible. Note that the container should not touch any walls or other objects, the entire weight of the container must rest on the scale for accurate weight measurement. The scale is dimensioned so that its placement under the container 12 will not compromise the stability of the container.

Figure 4:
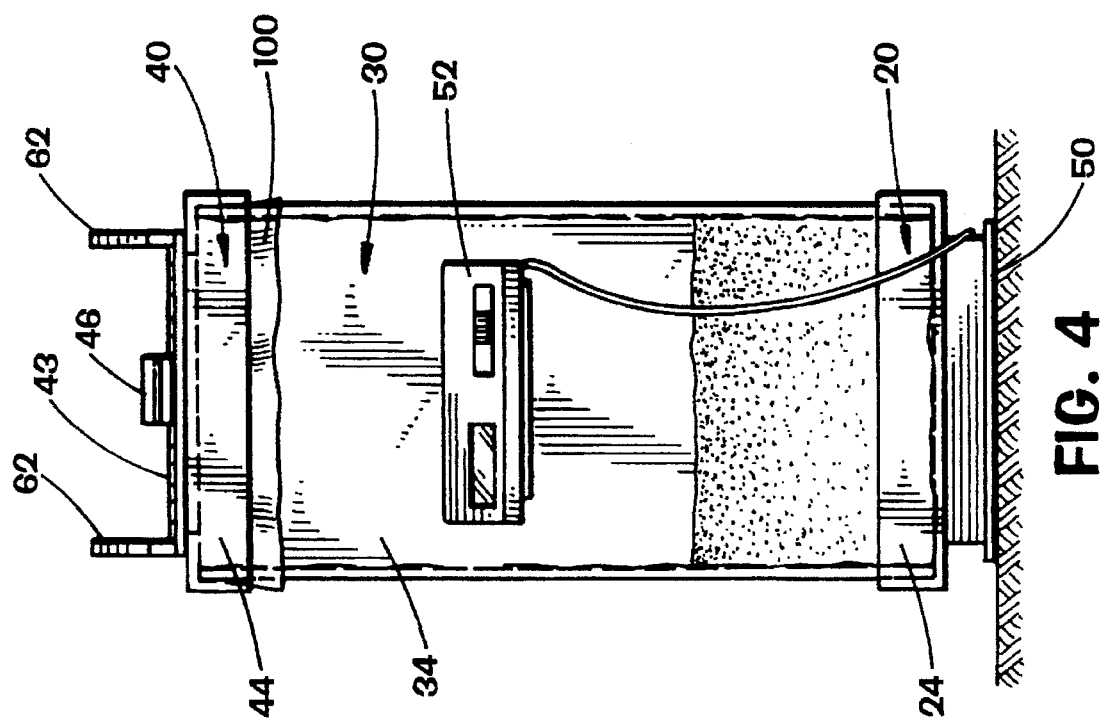
FIG. 4 is a front view of the assembled apparatus.

FIG. 4 is a front view of the assembled apparatus. The disclosed apparatus could also be used when filling disposable bags with products other than hazardous waste. For example, it may be used with many products which are sold by weight such as flour, sand, animal feed, and many others. It is also obvious that this apparatus could be adapted for use in filing other containers such as boxes, cans, or plastic drums.

There is thereby provided by the apparatus 10 of the present invention a system which allows the weight of hazardous waste entering a disposable plastic bag to be monitored while the plastic bag is being filled. Additionally, the disclosed invention holds a disposable plastic bag 100 without putting undue tear strain on the bag thus allowing the disposable plastic bag 100 to be safely filled to its optimum capacity.

While the hazardous waste disposal system of the present invention has been disclosed by reference to its preferred embodiment, those of ordinary skill in the art will understand that numerous changes and modifications may be made to the disclosed system without departing from the scope of the invention. Such changes and modifications are to be included within the scope of the appended claims.

I claim the following:

1. A hazardous waste disposal apparatus comprising:
    a scale having a digital readout display and a capacity for accurate measurement of a predetermined weight of hazardous waste;
    a clear acrylic container for holding a disposable bag without placing tear strain on said disposable bag, said clear acrylic container further comprising:
        a base having means for mounting said base to said scale;
        a detachable body having an open top end and an open bottom end, said open bottom end of said body constructed and arranged to slidably fit within said base; and
        a detachable cover constructed and arranged to slidably fit over said open top end of said body, said cover having an opening through which waste may be placed into the disposable bag and a hinged lid connected to said cover to temporarily close said opening.

2. A hazardous waste disposal apparatus as recited in claim 1 further comprising at least one mechanical stop for holding said lid open.

\* \* \* \* \*